United States Patent [19]

Schmitt et al.

[11] 4,212,962

[45] Jul. 15, 1980

[54] EPSILON-CAPROLACTAM BLOCKED POLYISOCYANATES

[75] Inventors: Karl Schmitt; Josef Disteldorf, both of Herne; Felix Schmitt, Wanne-Eickel, all of Fed. Rep. of Germany

[73] Assignee: Veba-Chemie Atkiengesellschaft, Gelsenkirchen-Buer, Fed. Rep. of Germany

[21] Appl. No.: 881,996

[22] Filed: Feb. 28, 1978

Related U.S. Application Data

[63] Continuation of Ser. No. 785,153, Apr. 6, 1977, abandoned, which is a continuation of Ser. No. 630,573, Nov. 10, 1975, abandoned, which is a continuation of Ser. No. 441,785, Feb. 12, 1974, abandoned, which is a continuation-in-part of Ser. No. 223,700, Feb. 4, 1972, Pat. No. 3,822,240.

[30] Foreign Application Priority Data

Feb. 8, 1971 [DE] Fed. Rep. of Germany ....... 2105777

[51] Int. Cl.² .................... C08G 18/80; C07D 211/40
[52] U.S. Cl. ...................................... 528/45; 546/188
[58] Field of Search ......................... 528/45; 546/188

[56] References Cited

U.S. PATENT DOCUMENTS

| | | | |
|---|---|---|---|
| 3,245,961 | 4/1966 | Fetscher et al. ...................... 528/45 |
| 3,660,359 | 5/1972 | Labana .......................... 260/77.5 CR |
| 3,676,402 | 7/1972 | Matsui et al. ................... 260/75 NC |
| 3,676,405 | 7/1972 | Labana .......................... 260/77.5 CR |
| 3,770,703 | 11/1973 | Gruber et al. ................ 260/77.5 TB |
| 3,808,160 | 4/1974 | Steinwetz ..................... 260/77.5 TB |
| 3,819,586 | 6/1974 | Rudolph et al. ............. 260/77.5 TB |
| 3,867,347 | 2/1975 | Felber et al. ................. 260/77.5 TB |

*Primary Examiner*—H. S. Cockeram
*Attorney, Agent, or Firm*—Sprung, Felfe, Horn, Lynch & Kramer

[57] ABSTRACT

Isophorone diisocyanate and reaction products of isophorone diisocyanate with polyols are substantially completely blocked with ε-caprolactam. The reaction product of isophorone diisocyanate and a polyol contains at least two isocyanate groups.

3 Claims, No Drawings

EPSILON-CAPROLACTAM BLOCKED POLYISOCYANATES

This is a continuation of application Ser. No. 785,153, now abandoned, filed Apr. 6, 1977, which is a continuation of application Ser. No. 630,573, filed Nov. 10, 1975, now abandoned, which, in turn, is a continuation of application Ser. No. 441,785, filed Feb. 12, 1974, now abandoned, which, in turn, is a continuation-in-part of application Ser. No. 223,700, filed Feb. 4, 1972, now U.S. Pat. No. 3,822,240, issued July 2, 1974.

BACKGROUND

The manufacture of masked polyisocyanates is known and is described in Houben-Weyl, "Methoden der organischen Chemie," volume XIV/2, pages 61–70. Tertiary alcohols, phenols, acetoacetic ester, malonic acid ester, acetylacetone, phthalimide, imidazol, hydrogen chloride, cyanogen water and ε-caprolactam are known as blocking-, coating- or masking agents. These masked isocyanates have the unique ability to react like isocyanate at elevated temperatures.

The more acid the hydrogen atoms of the masking group is, the easier the splitting off. Contrary to the free polyisocyanates, with masked isocyanates there can be made mixtures with hydroxyl-group-containing substances and solvents. without a reaction taking place during mixing or dissolving at relative low temperature, i.e., below the splitting (i.e. unblocking) temperature.

Thus, one is in a position with masked polyisocyanates to produce storable mixtures with hydroxyl-group-containing products, such as higher molecular polyesters or polyethers, which only at higher temperature, i.e, at or above the splitting temperature of the adducts, result in a desired isocyanate reaction. They are of considerable economical important for the production of elastomeric products via storable intermediate as well as for the production of coatings, particularly powder coatings, for metal coatings, etc.

However, many of these masked polyisocyanates, when used as cross-linking agents for terminal hydroxyl-group-containing polymers in a specific field, show an unsatisfactory behavior in actual use or they are excluded from this field of application because of the toxicity of the splitting products.

SUMMARY

The object of this invention is a 3-isocyanatomethyl-3,5,5-trimethylcyclohexylisocyanate or reaction product of 3-isocyanatomethyl-3,5,5-trimethylcyclohexylisocyanate with polyols each practically completely blocked with ε-caprolactam. In the latter case, polyisocyanate and polyol are used in such quantity ratios that the resulting product before blocking contains at least 2 isocyanate groups.

DESCRIPTION 3-isocyanatomethyl-3,5,5-trimethylcyclohexylisocyanate is also known as isophorone diisocyanate and by the initials "IPDI".

These new compounds are characterized by very special properties. In addition, they do not have the disadvantages described above. The blocked, cycloaliphatic polyisocyanates can be produced in the melt as well as in solution by adding the blocking agent to the isocyanate below the splitting temperature. The blocking agent is used in stoichiometric quantity or in slight excess. The addition proceeds exothermically. However, it is necessary after subsidence of the exothermic peak to maintain the reaction medium at elevated temperature for some time, in order to continue the reaction up to a yield of 99%.

By the use of catalysts, the addition to the blocked isocyanate in case of stoichiometric quantities of material can be increased to yields of 99.5%. The masking of the isocyanate groups should have taken place advantageously to about 99%, because otherwise during the later homogenization of the entire lacquer binding agent, there can result cross-linkages and thus portions which are difficult to melt or not at all, which prevent the formation of a perfect lacquer surface during the baking process.

This addition can be accelerated by way of catalysts of the type of the tertiary amines, for example triisobutylamine, triethylenediamine, and the like. In a number of cases, Na-methylate can also be used advantageously as catalysts.

For blocking and use in accordance with the instant invention, 3-isocyanatomethyl-3,5,5-trimethylcyclohexylisocyanate, which is also termed isophoronediisocyanate, is suitable as cycloaliphatic polyisocyanate. Also suitable are the reaction products of the named cycloaliphatic polyisocyanate with polyols, whereby polyisocyanate and polyol are used in such quantity ratios that the resulting product contains at least 2 isocyanate groups.

Suitable polyols are, for example, diols and triols, for example ethylene glycol, propylene glycols, such as 1,2-and 1,3-propanediol, 2,2-dimethylpropanediol-(1,3), butanediols, such as butanediol-(1,4), hexanediols, for example hexanediol-(1,6), 2,4,4-trimethylhexanediol-(1,6), 2,2,4-trimethylhexanediol-(1,6), heptanediol-(1,7), octadecene-9,10-diol-(1,12), thiodiglycol, octadecanediol-(1,18), 2,4-dimethyl-2-propylheptanediol-(1,3), butene- or butine diol-(1,4), diethylene glycol, triethylene glycol, trans- and cis-1,4-cyclohexanedimethanol, 1,4-cyclohexanediols, glycerin, hexane-triol-(1,2,6), 1,1,1-trimethylol propane and 1,1,1-trimethylolethane. Also, mixtures of the above compounds can be used.

Compounds of the type according to the invention are excellent cross-linking agents for terminal hydroxyl-group-containing polymers and pre-polymers. This characteristic is particularly advantageous in the case of non-blocked, solvent-free pulverulent coatings.

The preparation of isocyanates blocked with ε-caprolactam is described in the following examples.

EXAMPLE 1

3 moles (667 g) of 3-isocyanatomethyl-3,5,5-trimethylcyclohexylisocyanate (in short: isophorone diisocyanate or IPDI) and 6 moles (678 g) of ε-caprolactam were slowly heated to approx. 100° C. in a flask while stirring. As a result of the exothermic addition, the temperature rose temporarily to approx. 140° C. For completion of the reaction, the reaction mixture was maintained between 100° and 120° C. for another 2–3 hours. The product had the following chemical and physical properties:

| | |
|---|---|
| Molecular weight: | approx. 440 g/mole |
| Content of free isocyanate: | 0.4% NCO |
| Content of blocked isocyanate: | 18.5% NCO |
| Splitting temperature: | approx. 175° C. |
| Melting point: | 53°–55° C. |

EXAMPLE 2

(a) Preparation of the trimethylolpropane adduct of IPDI 3 moles of isophorone diiocyanate (667 g) together with 1,2 g of di-n-butyl-tin-dilaurate were placed as catalyst into a stirring flask. 141 g of trimethylolpropane (TMP) were idssolved in 434 g of ethylglycolacetate at about 50° C. and were kept in a heated vessel at about 50° C. (At lower temperature, solubility is exceeded, and it may result in crystallization. However, the system is strongly inclined to form upper-saturated solutions.).

From the heated vessel, approximately 20% of the TMP-solution were continuously added per hour to the diisocyanate under stirring. Due to the danger of crystallization, the TMP-solution had to flow directly into the strongly agitated reaction mixture. During the entire reaction, the temperature of the reaction mixture was between 18° and 25° C. In order to remove the heat liberated during the urethane formation, cooling had to be applied during the entire reaction time. After approx. 5 hours, the components were completely combined in the reaction vessel. For the completion of the reaction, it was stirred at 20° C. for approximately another 2 hours.

The 65% solution of this adduct is ethylglycolacetate had an isocyanate content of 9.35% NCO.

(b) Blocking of the trimethylolpropane adduct of the IPDI with ε-caprolactam 800 g of the solution of the trimethylol propane adduct of the IDPI in ethylglycol acetate, 202 g of ε-caprolactam and 448 g of ethylglycol acetate were slowly heated to 100° C. After approx. 2 hours, the temperature was increased to 120° C. After another hour, the content of free isocyanate had dropped to approx. 0.3%, so that the reaction had to be stopped. The low-viscous solution was cooled to room temperature and the solid, masked isocyanate adduct was precipitated with petroleum ether in that 300 g of the solution were ground with 1.5 liters of petroleum either in a 3 liter ball mill for several hours. The fine, white powder was easily separated by means of filtration. The adhering petroleum ether was removed from the substance in the oil pump vacuum. The powder had the following chemical and physical properties:

| | |
|---|---|
| Content of free isocyanate: | 0.5% NCO |
| Content of blocked isocyanate: | approx. 10% NCO |
| Splitting temperature | approx. 180° C. |
| Melting temperature: | 112°–118° C. |

EXAMPLE 3

12 moles (2664 g) of isophorone diisocyanate and 6 moles of trimethylhexanediol-(1,6) were mixed in a suitable stirring flask and slowly heated to approx. 70° C. At this temperature, the addition of the isocyanate to the diol set in under considerable evolution of heat. The reaction vessel was cooled in an ice bath during the addition, so that the temperature of the reaction mixture only rose to approx. 100° C. Afterwards, for the completion of the reaction, it was heated at 100° C. for another 2 hours. The NCO content then amounted to 14.0% (theoretically 13.9%).

It was then cooled to 80%C and the stoichiometric amount of ε-caprolactam corresponding to the content of isocyanate was added. Due to the also exothermic reaction, the temperature increased to 105° C. After 5 hours, the high-viscous melt was post-treated at 100° C. and then cooled to room temperature. The almost colorless solid material had a softening point of approx. 85° C. and a NCO content of 0.29%.

EXAMPLE 4

4 moles (889 g) of isophorone diisocyanate (IPDI) were made to react with 1.1 moles (117 g) of diethyleneglycol and 1.1 moles (114 g) of 2,2-dimethylpropandiol-1,3 at temperatures of 100° to 150° C. After the addition had taken place to form the di-isocyanato-urethane adduct, a content of free NCO groups of approximately 13,5 percent by weight was established. In the second stage the isocyanate groups were converted into the blocked form by reaction with 407 g of ε-caprolactam at temperatures of 100° to 120° C. This operation was concluded after about 3 hours.

The blocked polyisocyanate was characterized by the following chemical and physical characteristics:

| | |
|---|---|
| Content of free isocyanate groups: | 0.2% by weight NCO |
| Content of blocked isocyanate groups: | 9.7% by weight NCO |
| Splitting temperature: | 175° C. |
| Glass conversion temperature (DTA) | 48° to 65° C. |
| Melting intervall (according to Kofler): | 80° to 95° C. |
| DTA = differential thermoanalysis | |

EXAMPLE 5

3 moles (667 g) of isophorone diisocyanate (IPDI) and 2 moles (212 g) of diethyleneglycol were subjected to the addition reaction by thermal stimulation in the temperature range from 80° to 120° C. to form the diisocyanato-urethane adduct. Then the free NCO groups of this adduct were converted into the blocked form at 100° to 120° C. with 2 moles (226 g) of ε-caprolactam.

The product showed the following characteristics:

| | |
|---|---|
| Content of free isocyanate groups: | 0.2% by weight NCO |
| Content of blocked isocyanate groups: | 7.6% by weight NCO |
| Splitting temperature: | 175° C. |
| Glass conversion temperature (DTA) | 53° to 68° C. |
| Melting intervall (according to Kofler): | 79° to 90° C. |

What is claimed is:

1. Epsilon-caprolactam blocked polyisocyanates in particulate form, said polyisocyanates being selected from the group of isophorone diisocyanate and the reaction product of isophorone diisocyanate and a polyol, said reaction product containing at least two isocyanate groups.

2. Blocked polyisocyanate of claim 1 wherein said polyol is selected from the group of ethylene glycol, propylene glycols, butanediols, hexanediols, heptanediol, octadecene-9,10-diol-(1,12), octadecanediol-(1,18), 2,4-dimethyl-2-propylheptanediol-(1,3), butenediol-(1,4), diethylglycol, triethylglycol, trans-1,4-cyclohexanedimethanol, 1,4-cyclohexanediols, glycerine, hexanetriol-(1,2,6) and 1,1,1-trimethylol propane.

3. Urethane forming particulate coating composition comprising the blocked polyisocyanates of claim 1.

* * * * *

UNITED STATES PATENT AND TRADEMARK OFFICE
CERTIFICATE OF CORRECTION

PATENT NO. : 4,212,962
DATED : July 15, 1980
INVENTOR(S) : KARL SCHMITT, JOSEF DISTELDORF and FELIX SCHMITT It is certified that error appears in the above—identified patent and that said Letters Patent is hereby corrected as shown below:

In the cover page, under the caption "References Cited U.S. Patent Documents" the 6th name from the top should be --Steinmetz-- instead of "Steinwetz"

Signed and Sealed this

Twenty-eighth Day of October 1980

[SEAL]

Attest:

SIDNEY A. DIAMOND

*Attesting Officer* — *Commissioner of Patents and Trademarks*